(12) United States Patent
Yang et al.

(10) Patent No.: US 9,290,582 B2
(45) Date of Patent: Mar. 22, 2016

(54) B CELL ACTIVATING FACTOR ANTAGONIST AND PREPARATION METHOD AND USE THEREOF

(75) Inventors: Li Yang, Chengdu (CN); Yuquan Wei, Chengdu (CN)

(73) Assignees: CSPC ZHONGQI PHARMACEUTICAL TECHNOLOGY (SHIJIAZHUANG) CO., LTD., Shijiazhuang (CN); SICHUAN UNIVERSITY, Chengdu (CN)

( * ) Notice: Subject to any disclaimer, the term of this patent is extended or adjusted under 35 U.S.C. 154(b) by 251 days.

(21) Appl. No.: 13/699,903

(22) PCT Filed: May 26, 2011

(86) PCT No.: PCT/CN2011/074687
§ 371 (c)(1),
(2), (4) Date: Dec. 18, 2012

(87) PCT Pub. No.: WO2011/147320
PCT Pub. Date: Dec. 1, 2011

(65) Prior Publication Data
US 2013/0089549 A1   Apr. 11, 2013

(30) Foreign Application Priority Data
May 26, 2010   (CN) .......................... 2010 1 0183905

(51) Int. Cl.
| | |
|---|---|
| C07K 19/00 | (2006.01) |
| C07K 14/47 | (2006.01) |
| C07K 14/705 | (2006.01) |
| A61K 38/00 | (2006.01) |
| A61K 48/00 | (2006.01) |
| A61K 31/7088 | (2006.01) |

(52) U.S. Cl.
CPC .............. *C07K 19/00* (2013.01); *A61K 31/7088* (2013.01); *C07K 14/4703* (2013.01); *C07K 14/70578* (2013.01); *A61K 38/00* (2013.01); *A61K 48/005* (2013.01); *C07K 2319/00* (2013.01); *C07K 2319/30* (2013.01)

(58) Field of Classification Search
CPC ............ A61K 30/20; A61K 47/48246; A61K 39/0008; C07K 19/00; C07K 2319/30; C07K 2319/00; C07K 16/241; C07K 14/70578
See application file for complete search history.

(56) References Cited

U.S. PATENT DOCUMENTS

| | | |
|---|---|---|
| 2005/0070689 A1 | 3/2005 | Dixit et al. |
| 2010/0143352 A1 | 6/2010 | Chan et al. |
| 2010/0280227 A1 | 11/2010 | Ambrose et al. |

FOREIGN PATENT DOCUMENTS

| | | |
|---|---|---|
| CN | 1636067 A | 7/2005 |
| CN | 1835972 A | 9/2006 |
| CN | 101120021 A | 2/2008 |
| CN | 101851278 A | 10/2010 |

OTHER PUBLICATIONS

Wang Y, et al Construction of a eukaryotic vector containing human TACI-linker-BR3-IgGFc double receptor fusion gene and its expression in COS-7 cells. Acad. J. Sec. Mil. Med. Univ., 2006, VOl. 27(11), p. 1190, abstract only.*
English translation for CN101851278, downloaded Aug. 24, 2013.*
Mickle, J.E., et al. Genotype-phenotype relationships in cystic fibrosis. Medical Clinics of North America, 2000, vol. 84(3), p. 597-607.*
Wells, J.A. Additivity of mutational effects in proteins. Biochemistry, 1990, vol. 29(37), p. 8509-8517.*
Wang, et al., "Construction of a eukaryotic vector containing human TAC1-linker-BR3-IgGFc double receptor fusion gene and its expression in COS-7 cells", Acad. J. Sec. Mil. Med. Univ., vol. 11, pp. 1190-1195 (2006).
International Search Report for PCT/CN2011/074687 dated Sep. 8, 2011.
Moore et al., "BLyS: Member of the Tumor Necrosis Factor Family and B Lymphocyte Stimulator", Science, vol. 285, pp. 260-263 (1999).
MacKay et al., "The TNF family members BAFF and APRIL: the growing complexity", Cytokine & Growth Factor Reviews, vol. 14, pp. 311-324 (2003).
Schneider et al., "BAFF, a Novel Ligand of the Tumor Necrosis Factor Family, Stimulates B Cell Growth", J Exp Med, vol. 189, No. 11, pp. 1747-1756 (1999).
Sutherland et al, "Targeting BAFF: Immunomodulation for autoimmune diseases and lymphomas", Pharmacology & Therapeutics, vol. 112, pp. 774-786 (2006).
Scapini et al., "G-CSF-stimulated Neutrophils are a Prominent Source of Functional BLyS", J Exp Med, vol. 197, pp. 297-302 (2003).

(Continued)

*Primary Examiner* — Robert Landsman
*Assistant Examiner* — Bruce D Hissong
(74) *Attorney, Agent, or Firm* — Caesar Rivise, PC (57) ABSTRACT

The present invention relates to the field of genetic engineering drugs, particularly to a novel B cell activating factor (BAFF) antagonist and use thereof. The technical problem to be solved by the invention is to find a new and effective selection for the prevention and treatment of autoimmune diseases. The B cell activating factor receptor antagonist is mainly obtained by the fusion of the domain 2 binding BAFF in TACI receptor and the domain binding BAFF in Br3 receptor, and it also can be fused with a Fc segment of IgG1 to obtain a new fusion protein molecule. Experiments indicate that said new fusion protein molecule has the function of BAFF antagonist, which can treat the autoimmune diseases, and supply a new and effective selection for the prevention and treatment of the autoimmune diseases.

19 Claims, 7 Drawing Sheets

(56) References Cited

OTHER PUBLICATIONS

Hymowitz et al., "Structures of APRIL-Receptor Complexes: Like BCMA, TACI Employs Only a Single Cysteine-Rich Domain for High Affinity Ligand Binding", J. Biol. Chem., vol. 280, pp. 7218-7227 (2005).

Kim et al., "Crystal structure of the BAFF-BAFF-R complex and its implications for receptor activation", Nature Structural Biology, vol. 10, No. 5, pp. 342-348 (2003).

* cited by examiner

B CELL ACTIVATING FACTOR ANTAGONIST AND PREPARATION METHOD AND USE THEREOF

TECHNICAL FIELD

The present invention relates to the field of genetic engineering drugs, particularly to a novel B cell activating factor (BAFF) antagonist, preparation method and use thereof.

BACKGROUND ART

The autoimmune diseases, such as Rheumatoid arthritis (RA), Systemic lupus erythematosus (SLE), Sjögren's syndrome (sjogren syndrome) and so on, are closely related to the excessive proliferation of B cell or plasmocyte of the body and humoral immune activation.

B cell activating factor (BAFF), also known as BLyS, TALL-1, THANK, zTNF4 or TNFSF-13B, which is a member of the TNF family, which was discovered in 1999[1], initiates downstream signaling pathways and regulates of B cell's survival, maturation and differentiation[2] by binding to its homologous receptors. BAFF and other three ligands (APRIL, EDA and TWEAK) belong to the same subtype, and have the similar function and structure characteristics[3]. BAFF, which has membrane-bound and soluble forms, is a type II transmembrane protein. The soluble form is composed of 152 amino acids, and is produced following proteolysis of the membrane-bound form (which has 285 amino acids) between R133 and A134 by proteases. This process is regulated at both a stimulus and cell type level[3]. Under normal physiological conditions, soluble BAFF exists as a trimer and expresses the biological activity[4]. BAFF is mainly produced by peripheral blood mononuclear cells (PBMNCs), including the macrophages, monocytes and dendritic cells in the spleen and lymph nodes[5].

The three receptors of BAFF: BCMA (B cell maturation antigen), TACI (transmembrane activator and CAML interactor) and BAFF-R (BAFF receptor, Br3), which is disclosed in prior art are all type III transmembrane protein. BAFF and APRIL are capable of binding to TACI and BCMA with high affinity, and BAFF can also bind to BAFF-R. Extracellular domain of TNF receptor contains multiple cysteine-rich domains (CRD), and each CRD is comprised of three disulfide bonds which are formed by six cysteine residues. BCMA has single CRD, and compared to BCMA, TACI contains two typical CRD: CRD1 and CRD2, wherein only CRD2 involves ligand binding (TACI (aa.70-104): see SEQ ID NO:8)[6]. Br3 contains only one CRD which consists of 4 cysteine residues (Br3 (aa.18-35): see SEQ ID NO:9), and binding domain to BAFF is reduced to 26 amino acids[7].

Besides the function of promoting B cell survival, BAFF also plays an important role of regulation in the maintenance of the germinal center reaction, isotype switching, T cell activation and so on. BAFF has the effect on T cell activation, so it may play an important role in pathogenesis of autoimmune diseases. Therefore, BAFF and its receptors as novel targets for treatment of autoimmune diseases have received wide concern. The specific antagonist of BATF (including soluble receptor TACI-Fc, Br3-Fc or anti-BAFF antibodies and so on) can inhibit the biological activity of BAFF, thereby playing a role in the treatment of autoimmune disease, such as rheumatoid arthritis (RA), Sjögren's syndrome, systemic lupus erythematosus (SLE) and so on. At present, in March 2011, FDA had approved fully human anti-BAFF monoclonal antibody Belimumab (trade name: Benlysta) listed, indications for SLE, which become the first listed new drugs for treating lupus in more than 50 years, and the treatment for RA has also entered into clinical trial phase III; research on soluble receptor TACI-Fc treating SLE and RA has already entered into phase II/III clinical trial.

DISCLOSURE OF THE INVENTION

The technical problem to be solved by the present invention is to find new effective choice for the prevention and treatment of autoimmune diseases, in particular to prevent and treat autoimmune diseases by antagonizing BAFF.

To solve the technical problem, the technical solution of the present invention is to provide a novel B cell activating factor antagonist. Said B cell activating factor antagonist is a kind of protein.

In particular, the structure of said B cell activating factor antagonist is:

(1) fusion protein containing the following structural domains: the domain obtained by the fusion of CDR2 domain binding to BAFF in TACI receptor and CDR domain binding to BAFF in Br3 receptor.

Or (2) protein which is obtained by substituting and/or deleting and/or adding at least one amino acid in the amino acid sequence of the fusion protein defined in (1), having the same or similar function with the fusion protein as defined in (1). The structural domain of B cell activating factor antagonist plays a major role in binding B cell activating factor.

Wherein, said B cell activating factor antagonist is:

(1): protein having amino acid sequence shown as SEQ ID NO:1.

Or (2): protein which is obtained by substituting and/or deleting and/or adding at least one amino acid in the amino acid sequence of the protein shown as SEQ ID NO:1, having the same or similar function with the protein shown as SEQ ID NO:1.

Further, said B cell activating factor antagonist is:

(1): protein, having the amino acid sequence which is connected with the amino acid sequence of Fc fragment of human immunoglobulin on the C-terminus of the amino acid sequence shown as SEQ ID NO:1.

Or (2): protein which is obtained by substituting and/or deleting and/or adding at least one amino acid in the amino acid sequence of the protein defined in (1), having the same or similar function with the protein as defined in (1).

Furthermore, said B cell activating factor antagonist is the protein whose amino acid sequence is shown as SEQ ID NO:2;

Or: the protein which is obtained by substituting and/or deleting and/or adding at least one amino acid in the amino acid sequence of the protein shown as SEQ ID NO:2, having the same or similar function with the protein shown as SEQ ID NO:2.

Because of adding Fc fragment of human immunoglobulin, the fusion protein prepared by genetic engineering manner exists in dimeric form.

Preferably, said B cell activating factor antagonist is the protein which is connected with signal peptide at N-terminal.

More preferably, said B cell activating factor antagonist is the protein that amino acid sequence is shown as SEQ ID NO:3;

Or: the protein which is obtained by substituting and/or deleting and/or adding at least one amino acid in the amino acid sequence of the protein shown as SEQ ID NO:3, having the same or similar function with the protein shown as SEQ ID NO:2.

The present invention not only provides said B cell activating factor antagonist which is protein essentially, but also provides the nucleotide sequences encoding said B cell activating factor antagonist.

Wherein, said nucleotide sequences encoding B cell activating factor antagonist is:

(1): nucleotide sequence or its degenerate sequence shown as SEQ ID NO:10;

Or (2): nucleotide sequence which is derived from substituting, deleting or adding at least one nucleotide in the amino acid sequence shown as (1), having the same or similar function with the nucleotide sequences encoding shown as SEQ ID NO:10.

Wherein, said nucleotide sequences encoding B cell activating factor antagonist is:

(1): nucleotide sequence or its degenerate sequence shown as SEQ ID NO:4;

Or (2): nucleotide sequence which is derived from substituting, deleting or adding at least one nucleotide in the amino acid sequence shown as (1), having the same or similar function with the nucleotide sequences encoding shown as SEQ ID NO:4.

Wherein, said nucleotide sequences encoding B cell activating factor antagonists is:

(1): nucleotide sequence or its degenerate sequence shown as SEQ ID NO:5;

Or (2): nucleotide sequence which is derived from substituting, deleting or adding at least one nucleotide in the amino acid sequence shown as (1), having the same or similar function with the nucleotide sequences encoding shown as SEQ ID NO:5.

The present invention also provides a gene vector containing said nucleotide sequence. Preferably, said gene vector is an expression vector which is capable of expressing said nucleotide sequence.

The present invention also provides a host cell containing said gene vector.

Further, the present invention also provides use of said B cell activating factor antagonist, or said nucleotide sequence, or said gene vector for manufacturing a medicament for treatment of autoimmune disease.

further, the present invention provides a medicine for preventing or treating autoimmune disease, wherein, said B cell activating factor antagonist, or said nucleotide sequence, or said gene vector is the main active ingredient.

Wherein, said autoimmune disease mainly refers to rheumatoid arthritis, systemic lupus erythematosus, Sjogren syndrome (Sjögren syndrome).

For a better implement of the present invention, it also provides a method for preparation of said B cell activating factor antagonist. The method comprises the following steps: loading the genes encoding B cell activation factor antagonist into expression vector operatively, transferring the expression vector into host, cultivating and proliferating the host, and obtaining B-cell activating factor antagonist by isolation and purification the host and/or its culture supernatant.

Wherein, said expression vector in preparation method of said B-cell activating factor antagonist is a eukaryotic plasmid expression vector, adenovirus vector or adeno associated virus vector.

Wherein, said host in the preparation method of said B cell activating factor antagonist is eukaryotic cell.

Wherein, said isolation and purification method in the preparation method of said B-cell activation factor antagonist is: purifying the supernatant of large-scale cultivation of the host by Mab-Select gel column made by GE company and SP column chromatography, and then obtaining B cell activating factor antagonists.

Apparently, the expression vector in the above method may be a common eukaryotic expression vector, a variety of host cells commonly used in genetic engineering. The isolation and purification method can refer to the existing common method to obtain a relatively pure B cell activating factor antagonist of the present invention. The methods of loading the genes encoding B cell activation factor antagonist into expression vector operatively and transferring the expression vector into host can refer to a variety of gene engineering manual and the specific instruction of the vector and host cell.

The present invention designs and constructs BAFF antagonistic fragment that obtained by the fusion of the domain 2 (CRD2) binding BAFF in TACI receptor and the domain (CRD) binding BAFF in Br3 receptor and the (amino acid sequence shown as SEQ ID NO:1, coding by the nucleotide sequence shown as SEQ ID NO:10). In order to enhance its stability in vivo and prolong half-life, said fragment can be fused with Fc fragment of immunoglobulin to obtain a new fusion protein. For example, it can be fused with Fc fragments of IgG1, IgG2 or IgG4. In the embodiment of the present invention, fused it with Fc fragment of IgG1 to get a new fusion protein—named BAFF Trap (amino acid sequence shown as SEQ ID NO:2, coded by nucleotide sequence shown as SEQ ID NO:4), Experiments showed that it had the function of B cell activating factor antagonists. Of course, B cell activating factor antagonist in the present invention is a kind of protein, therefore, the main preparation method is to use genetic engineering method in prior art for fermentation. While conducting genetic engineering fermentation, in order to recover the product conveniently, generally the N-terminus of the coding sequence of the BAFF Trap are connected with various commonly used encoding nucleotide sequence of secretion signal peptide, such as human IL-2 signal peptide encoding nucleotide sequence (after adding the human IL-2 signal peptide, its amino acid sequence shown as SEQ ID NO:3, may be coded by nucleotide sequence shown as SEQ ID NO:5).

In the present invention, gene sequence, similar expression with "the nucleotide sequence in SEQ ID NO:1 which is substituted, deleted or added at least one nucleotide derivative sequence" generally refers to a nucleotide sequence which is encoded by the protein activity polypeptide encoded by SEQ ID NO:1 and its degenerate sequence. The degenerate sequence refers to the sequence in which one or more codons are replaced by degenerate codons encoded by same amino acid. Due to the degeneracy of the codons, the degenerate sequence that SEQ ID NO:1 homology is as low as about 89% can also encode sequence as same shown as SEQ ID NO: 1. In addition, the meaning of "the nucleotide sequence shown as SEQ ID NO:1 which is substituted, deleted, or added at least one nucleotide derivative sequence" also includes the nucleotide sequence hybridizing with SEQ ID NO:1 nucleotide sequence under moderately stringent condition, more preferably under highly stringent condition. The term also includes that the nucleotide sequence SEQ ID NO:1 homology is at least 80%, preferably at least 89%, more preferably at least 90%, most preferably at least 95%. Having the same function in the present invention refers to have the function of binding with the BAFF and antagonizing the biological activity of BATF.

The term "the nucleotide sequence in SEQ ID NO:1 which is substituted, deleted, or added at least one nucleotide derivative sequence" also includes the variant form of open reading frame sequence in SEQ ID NO:1 which can encode the protein having the same protein function as protein encoded by SEQ ID NO:1. These variant forms includes (but not limited to): deleting, inserting and/or substituting several nucleotides (typically 1 to 90, preferably 1 to 60, more preferably 1 to 20, most preferably 1 to 10), and adding several nucleotides (typically less than 60, preferably less than 30, more preferably less than 10, most preferably less than 5) at the 5' and/or 3' end.

In the present invention, the term "amino acid sequence which is derived from substituting and/or deleting and/or adding at least one amino acid in said amino acid sequence" includes but is not limited to deleting, inserting and/or substituting several amino acids (usually 1-50, preferably 1-30, more preferably 1-20, most preferably 1-10), adding one or several amino acids at the C-terminus and/or N-terminus (usually less than 20, preferably less than 10, more preferably less than 5). For example, when substituted by a similar performance amino, the function of said protein usually can not change. Another example, adding one or several amino acids at the C-terminus and/or N-terminal usually won't change the function of the protein. The term also includes the active fragments and active derivatives of said protein. The same function in the present invention refers to the function of binding with BATF and antagonizing BAFF biological activity.

The expression "amino acid sequence which is derived from substituting and/or deleting and/or adding at least one amino acid in said amino acid sequence" includes but not limited to replace up to 10 (i.e. one or several) amino acids, preferably up to 8 amino acids, more preferably up to 5 amino acids by similar property amino acids to form polypeptides, i.e. conservative variant polypeptides. Preferably, these conservative variant polypeptides are replaced according to Table 1.

TABLE 1

Amino acid substitution table

| The initial residue | Representative substituent | Preferred substituent |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also includes proteins or polypeptide analogues of the claim. The difference between the analogues and proprotein can be the difference in amino acid sequence, and it can also be the difference in modified form that do not affect the sequence, or both. These proteins include natural or induced genetic variants. Induced variants can be obtained by various techniques, such as random mutagenesis generated by irradiation or exposure to mutagens, and it can also be obtained by site directed mutagenesis or other known molecular biology techniques. Analogues also include the analogues containing a different natural L-amino acid residue (e.g., D-amino acid), as well as a non-naturally or synthetic amino acid (such as $\beta$, $\gamma$-amino acid). It should be appreciated that the proteins or peptides in the present invention is not limited to the representative proteins or polypeptides above-exemplified.

Modified (usually do not change the primary structure) forms include: a chemical derivatization forms of polypeptide in vivo or vitro, such as acetylation or carboxylation. Modification also includes glycosylation, such as the polypeptide obtained by glycosylation modification in the polypeptide synthesis and processing or in further processing steps produce a polypeptide. Said modification can be carried out by exposing the polypeptide to a kind of glycosylation enzyme (such as a glycosylation enzyme or deglycosylation enzyme of mammalian). The modified form also includes sequence that has phosphorylated amino acid residue (e.g. phosphotyrosine, phosphoserine, phosphothreonine). It also includes the modified polypeptide which can improve anti-proteolytic property or optimize solubility property.

The term "operably connected to" described in the present invention refers to: i.e. some portions of the linear DNA sequence are able to influence the activity of other portions of the same linear DNA sequence. For example, if the signal peptide DNA is expressed as a precursor, and participate in the secretion of the polypeptide, then the signal peptide (secretory leader sequence) DNA is operably connected to the polypeptide DNA; if start the transcription of promoter control sequence, then it is operably connected to encoding sequences; if the ribosome binding site is placed on the position that enable to translate, then it is operably connected to encoding sequence. Generally, "operably connected to" means adjacent, but for the secretory leader sequence means adjacent to the reading frame.

Beneficial effects of the present invention are: the present invention designs and the constructs fragment that obtained by the fusion of the domain 2 (CRD2) binding BAFF in TACI receptor and the domain (CRD) binding BAFF in Br3 receptor, in order to enhance its stability in vivo and prolong half-life, it could be fused with Fc fragment of immunoglobulin. For example, it can be fused with Fc fragments of IgG1, IgG2 or IgG4. In order to carry out better secretory expression, it can connect a signal peptide at its N-terminal, and thus it can obtain a series of new fusion protein molecules. The new type of B cell activating factor antagonists—BAFF Trap in the present invention can improve combined effect with BAFF greatly, reduce therapeutic dose, and improve on curative effect of autoimmune diseases. It provides a new effective choice for prevention and treatment of autoimmune diseases.

DESCRIPTION OF EMBODIMENT

The present invention is further described in the following embodiments with reference to the accompanying figures. In the following examples, experimental conditions which do not indicate specifically are well known to those skilled in the art in accordance with the conventional conditions, such as the conditions described in E.g. Sambrook J, Russell D W and 2001, Molecular Cloning: A laboratory manual (3$^{rd}$ ed), the Spring Harbor Laboratory Press, or the conditions recommended by the manufacturers.

Embodiment 1: Construction and Expression of BAFF Trap-Encoding Gene

1. The Method for Preparation of BAFF Trap-Encoding Gene

Using whole gene synthesis method to obtain cDNA fragment fused by TACI domain 2 and the Br3 domain (CRD), and containing the human IL-2 signal peptide sequence at the 5' end of the fragment.

Meanwhile, design the following primers to amplify IgG1 Fc fragment cDNA:

```
5' primer (SEQ ID NO: 6):
5' CGG GAT CCG ACA AAA CTC ACA CAT GCC 3'

3' primer (SEQ ID NO: 7):
5' AGC TTT GTT TAA ACT CAT TTA CCC GGA GAC AGG 3'
```

In order to insert PCR product into a cloning vector, BamH I sites was designed at 5' primer, and Pme I sites was designed at 3' primer.

Total RNA in human lymphocytes as a template, RT-PCR amplify IgG1 Fc fragment, the reaction conditions were as follows:

After RT-PCR reaction mixture denaturation for 30 minutes at 50° C., reaction was carried out in the following conditions:

The reverse transcription reaction: denaturation at 94° C. for 30 seconds; anneal at 55° C. for 30 seconds; extension at 68° C. for 1 minute. Reaction for 10 cycles.

PCR reaction: denaturation at 94° C. for 30 seconds; anneal at 60° C. for 30 seconds; extension at 68° C. for 1 minute. Reaction for 25 cycles. Then extending it at 68° C. for other 12 minutes.

Figure 3:
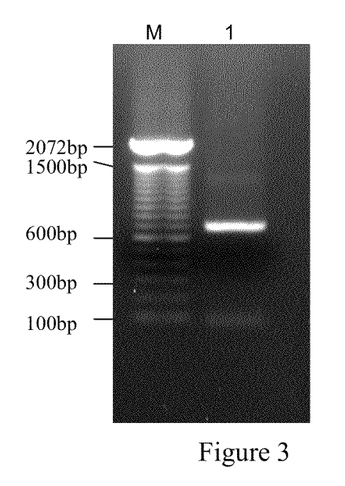
FIG. 3 shows the RT-PCR results of IgG1 Fc (1% Agarose gel electrophoresis). M: 100 bp DNA Ladder (Invitrogen); 1: RT-PCR product.

After completion of the reaction, detected the RT-PCR product by 1% agarose gel electrophoresis. Shown as FIG. 3, it could obtain a DNA fragment of the expected size (~700 bp).

Figure 1:
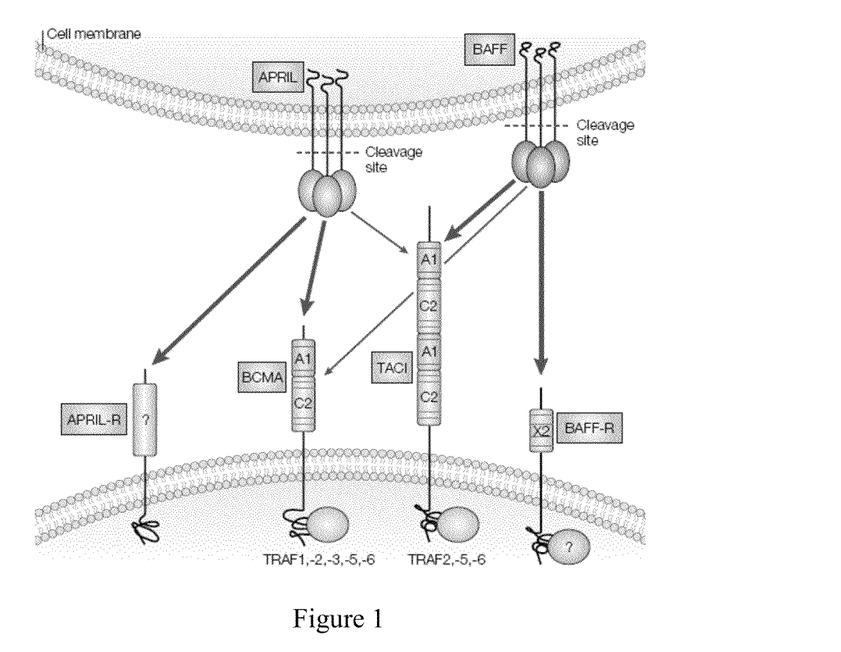
FIG. 1 shows an interaction schematic diagram of BAFF and its receptor, excerpted from *Nature Review the Immunology*, 2002, 2:465-475.
Figure 2:
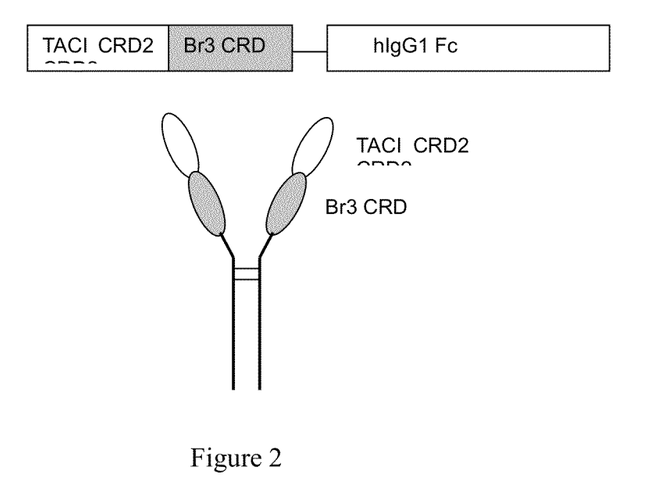
FIG. 2 shows a structural schematic diagram of BAFF Trap, due to adding Fc fragment, fusion protein exist easily in the form of dimer.

The nucleotide and protein sequences of the full-length BAFF Trap were shown as SEQ ID NO:5 and SEQ ID NO:3 respectively. Because of adding Fc fragment, fusion protein exists in the form of dimer by disulfide bond. The BAFF Trap structure diagram wshown as FIG. 2.

Figure 4:
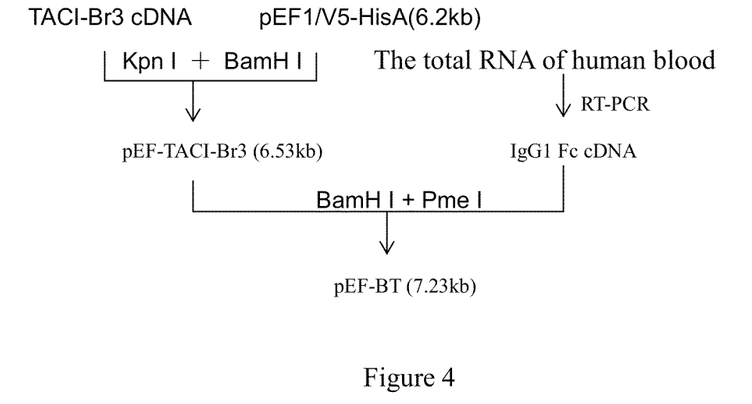
FIG. 4 shows a schematic diagram of the construction of recombinant plasmid pEF-BT.
Figure 5:
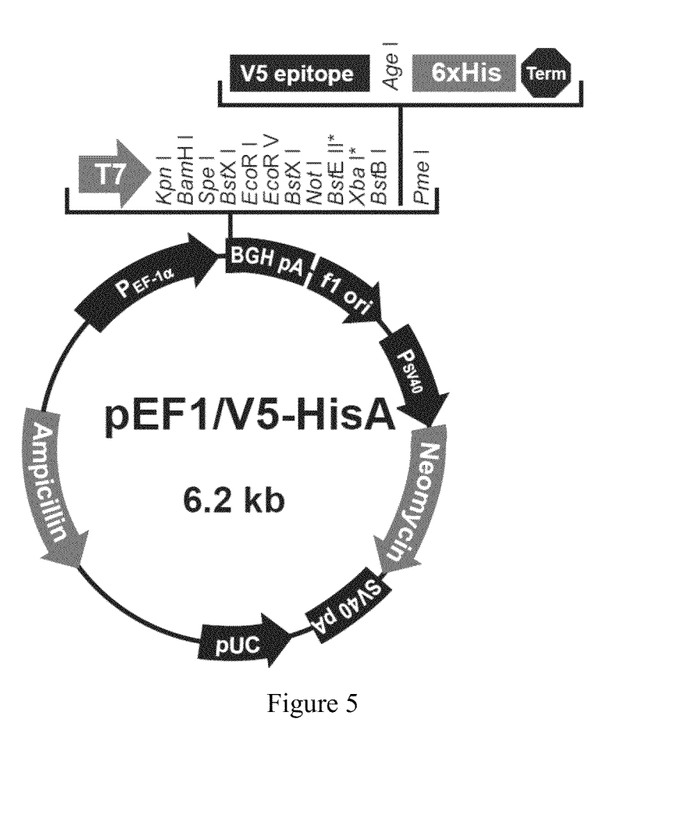
FIG. 5 shows a plasmid profile of eukaryotic expression vector pEF1/V5-His A.

2. Construction of the Recombinant Plasmid Containing of BAFF Trap-Encoding Gene As mentioned above, in the whole gene synthetic fragment (TACI-Br3), the Kpn I restriction sites was designed at 5' primer, the BamH I restriction sites was designed at 3' primer, so a cDNA fragment of the TACI-Br3 could be inserted directly into multiple cloning site Kpn I/BamH of eukaryotic expression vector pEF1/V5-HisA (purchased from Invitrogen Corp. of USA, its map shown as FIG. 5), IgG1 Fc fragment was inserted into the multiple cloning site BamH I/Pme I, and thus fusion fragment of BAFF Trap could be obtained. The building process wshown as FIG. 4.

2.1 Construction of Recombinant Plasmid pEF-TACI-Br3

Figure 6:
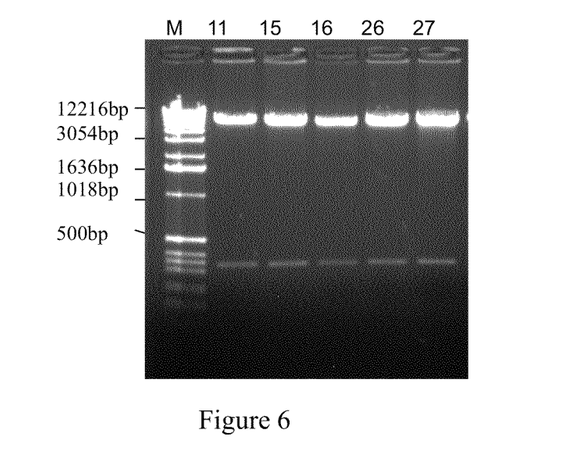
FIG. 6 shows the Kpn I/BamH I double digestion results of the recombinant plasmid pEF-TACI-Br3 (1% Agarose electrophoresis). M: 1 kb DNA Ladder (Invitrogen); 11, 15, 16, 26, 27 represent different clones respectively.

Inserted whole gene synthesis fragments TACI-Br3 into Kpn I/BamH I site of pEF1/V5-HisA, ligation product pEF-TACI-Br3 transformed E. coli JM109, randomly selected 28 clones and screened. No. 11, 15, 16, 26 and 27 clones were back cut by Kpn I/BamH I to obtain target fragment. Enzyme digestion results of recombinant plasmid pEF-TACI-Br3 were shown as FIG. 6. Choosing No. 26 clone for sequence analysis, if the sequence is correct, furthermore building fusion gene with IgG1 Fc.

2.2 Construction of Recombinant Plasmid pEF-BT

Figure 7:
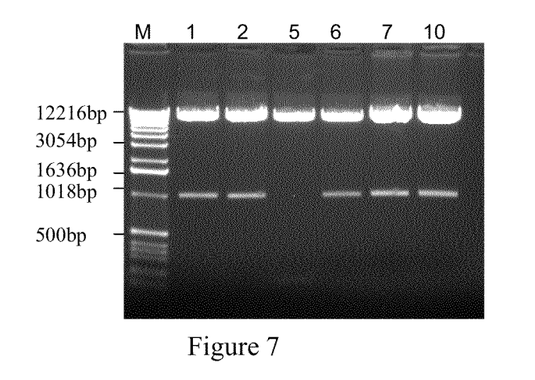
FIG. 7 shows the Kpn I/Pme I double digestion results of the recombinant plasmid pEF-BT (1% Agarose electrophoresis). M: 1 kb DNA Ladder (Invitrogen); 1, 2, 5, 6, 7, 10 represent different clones respectively.

Based on PEF-TACI-Br3 No. 26 clone, inserting IgG1 Fc fragment into BamH I/Pme I site, ligation product pEF-BT transforming into E. coli JM109, randomly selecting 12 clones for screening. Enzyme digestion results of recombinant plasmid pEF-BT were shown as FIG. 7. Back cutting No. 1, 2, 6, 7, 10 clone by using Kpn I/Pme I to obtain target fragment, sending No. 10 clone for DNA sequencing. The DNA sequencing result shows that the sequence of the target gene in the recombinant plasmid and BAFF Trap gene of design (TACI-Br3-IgG1 Fc) (i.e., SEQ ID NO:5) are consistency.

4. Screening and Identification of Stably Expressing Strain—CHO-BT of the Target Protein Took 5 microgram said recombinant plasmid pEF-BT by large scale preparation, transfected CHO-K1 cells (purchased from ATCC, USA) by using liposomes Lipofectamine-2000, passaging with ratio of 1:5 after two days, adding 0.4 mg/ml G418 (purchased from Invitrogen company, USA) to screening, colony formation was visible after 10 days. Randomly digesting 96 monoclones which have clearly separated edge and good cell condition, inoculating in six 24-well plate and culturing (first round screening).

After two days, took culture supernatant, detected the fusion protein expression by ELISA, choosing 24 positive expression clones to inoculating in a 24-well plate (second round screening) respectively. After culturing for 2 days, detecting the fusion protein expression of supernatant by ELISA, selected six clones which had higher expression: 1-B2, 1-B8, 1-D7, 1-E1, 2-D1, 2-F6, for further screening with limited dilution method.

Inoculated in 96-well plates respectively (1 cell/well/200 μL) (third round screening), after cells confluence (after about 8 days), detected fusion protein expression of the culture supernatants by ELISA, selected six clones which have higher expression and inoculated into 24-well plate. Until the cells confluence, inoculated 6-well plate, detected the expression of each clone by ELISA. The results were shown as Table 2.

TABLE 2

The expression of supernatant of subcloned of six clones in the third round screening after 48 hours by ELISA detection

| 1-B2 | A450 | 1-B8 | A450 | 1-D7 | A450 |
|---|---|---|---|---|---|
| 1-B2-4 | 0.968 | 1-B8-1 | 0.965 | 1-D7-4 | 0.632 |
| 1-B2-7 | 1.079 | 1-B8-2 | 1.051 | 1-D7-7 | 0.775 |
| 1-B2-8 | 0.369 | 1-B8-3 | 0.748 | 1-D7-10 | 0.758 |
| 1-B2-9 | 0.432 | 1-B8-5 | 0.639 | 1-D7-13 | 0.302 |
| 1-B2-11 | 0.751 | 1-B8-8 | 0.112 | 1-D7-14 | 0.456 |
| 1-B2-13 | 0.919 | 1-B8-11 | 0.357 | 1-D7-17 | 0.34 |
| 1-E1 | A450 | 2-D1 | A450 | 2-F6 | A450 |
| 1-E1-1 | 0.562 | 2-D1-2 | 0.256 | 2-F6-2 | 0.607 |
| 1-E1-3 | 0.929 | 2-D1-3 | 0.181 | 2-F6-3 | 0.873 |
| 1-E1-6 | 0.984 | 2-D1-4 | 0.187 | 2-F6-4 | 0.835 |
| 1-E1-7 | 0.948 | 2-D1-5 | 0.135 | 2-F6-5 | 0.352 |
| 1-E1-12 | 0.794 | 2-D1-9 | 0.178 | 2-F6-6 | 0.904 |
| 1-E1-16 | 0.593 | 2-D1-13 | 0.268 | 2-F6-7 | 0.281 |

Selected higher expression of 1-B8-1, 1-D7-7 and 1-E1-7 to scale-up culture, expanded into T75 square bottle, the supernatants was harvested after four days, adsorpted it by Pr.A-Sepharose, detected the expression of the fusion protein, the results showed that molecular weight of the purified protein and expected protein was the same, and verified it by Western Blot.

Took 1-B8-1, 1-D7-7,1-E1-7 respectively to inoculate into 96-well plate (1 cell/well/200 μL) (fourth round screening), after cells confluence (approximately after 10 days), detected fusion protein expression of culture supernatants by ELISA, three clones were homogeneous, the highest expression were amplified and conservation, named CHO-BT (1-B8-1), CHO-BT (1-D7-7), CHO-BT (1-E1-7), picked CHO-BT (1-E1-7) for the next expression and purification.

5. Increased Expression and Purification of Fusion Protein BAFF Trap (BT)

Figure 8:
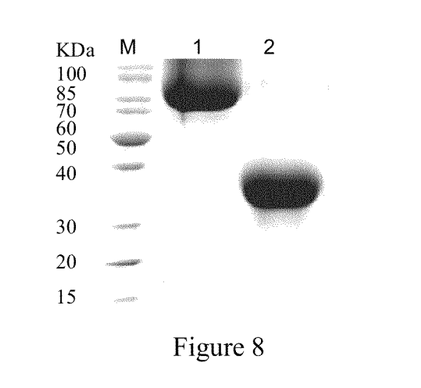
FIG. 8 shows an electrophoresis pattern of purified protein (12% SDS-PAGE). M: protein molecular weight standard; 1: non-reducing condition; 2: reducing condition.

After large-scale cultivation of the said screened CHO-BT (1-E1-7) cells, the supernatant was purified by gel MAB-Select (purchased from GE company, USA), then passed through SP column chromatography, after a two-step column chromatography, protein electrophoresis pattern was shown as FIG. 8. The results showed that the molecular weight of purified target protein under reducing condition was 38 kDa, under non-reducing condition was 76 kDa, existing in form of dimer, which were consistent with our expected. Purity of the purified protein could be more than 95%.

Embodiment 2 Identification and efficacy experiment of fusion protein BAFF Trap (BT)

1. Determination on Binding Constant of Fusion Protein BAFF Trap (BT) and BAFF

Using BIAcore T100 to detect binding capacity of BAFF Trap and BAFF in vitro conditions, the binding constant was analysis by BIAcore T100 Evaluation Software. Also, the standards of BAFF R-Fc and TACI-Fc were used as a control substance. Steps were as follows:

(1) Coupling: diluted BAFF Trap protein using HEPES standard solution initially, then diluted it to 2 μg/ml using 10 mM sodium acetate solution (pH=5.0), volume of 200 μl, manual injection 4 times for coupling, flow rate and time as routinely. Added quantitative standards of TACI-Fc and Br3-Fc into sodium acetate solution, the final concentration also was 2 μg/ml, volume of 200 μl, coupled and fixed it on the chip by using the same method.

(2) Binding assays: Gradient diluted BAFF standard using HEPES solution, at 1800 nm, 600 nm, and 200 nm, 66 nm and 22 nm, the volume was no less than 120 μl, cyclic loading, the contact time was 60 s, the dissociation time was 900 s, flow rate was 30 μl/min.

(3) Kinetic analysis: Analyzed coupling rate (Ka) and dissociation rate (Kd) using BIAcore T100 Evaluation Software, binding constant KD=Kd/Ka.

The results showed that: as compared to TACI-Fc and Br3-Fc, BAFF Trap had a stronger BAFF binding capacity, KD value was about 12.7 nM, and binding constants of TACI-Fc and Br3-Fc with BAFF were 14.8 nM and 34 nM respectively (table 3).

TABLE 3

The analysis on binding constant of BAFF Trap and BAFF

| | sample | | |
|---|---|---|---|
| | $K_D$(nM) | $K_a$ (M$^{-1}$s$^{-1}$) | $K_d$ (s$^{-1}$) |
| BAFF Trap | 12.7 | $1.10 \times 10^{-4}$ | $1.415 \times 10^{-4}$ |
| TACI-Fc | 14.8 | $5.15 \times 10^{3}$ | $7.630 \times 10^{-5}$ |
| Br3-Fc | 34.0 | $1.99 \times 10^{4}$ | $6.790 \times 10^{-4}$ |

2. Identification on Cell Binding of Fusion Protein BAFF Trap (BT) In Vitro

Raji cells (purchased from ATCC, USA) are human B cell line for high expression BAFF receptor (TACI and Br3), which are used to detect the combination of the BT competitive antagonism BAFF. Raji cells were harvested in the logarithmic growth phase, adding BT protein and anti-TACI antibody/anti Br3 antibody of different concentrations, incubated for 1 hour at room temperature, added FITC-labeled second antibody after washing, and incubated in the dark at room temperature for half an hour, detected by upflow cytometric after washing, results were shown as Table 4. (Wherein, hIgG contained human IgG1 Fc fragment, as the contents of protein group)

TABLE 4

Flow test results of BT blocking Raji cell surface BAFF receptor

| | BAFF acceptor | |
|---|---|---|
| proportion of positive fluorescent cell | TACI | Br3 |
| first antibody | 85.2% | 34.3% |
| first antibody + BT(1 μg) | 71% | 22.6% |
| first antibody + BT(10 μg) | 58.5% | 14.6% |
| first antibody + BT(100 μg) | 41.1% | 15.2% |
| first antibody + hIgG(μg 100) | 80.5% | 32.9% |

The results showed that, BT could competitively inhibit the combination of antibody and the BAFF receptors—TACI and Br3 on Raji cells, and showed a dose dependency. It means that in vitro experiment, BT can be used as an antagonist inhibiting the binding of BAFF and its cell surface receptor.

3. Therapeutic Effect of Fusion Protein BAFF Trap (BT) in Rat Rheumatoid Arthritis Model.

Study Therapeutic Effect of BT In Vivo by Rat Adjuvant-Induced Arthritis Model (AIA)

Experimental methods: 6-8 weeks old female Lewis rats were injected intradermally in the base of the tail with 100 μL incomplete Freund's adjuvant containing 5 mg/ml inactivated BCG, the rats in the control group without processing. Onset rats were randomly divided into three groups for treatment: saline group, hIgG group, fusion protein BT group (n=10), intraperitoneal administration of 100 μg/100 μl/per, only administration twice every week. (hIgG group containing the human IgG1 Fc fragment, using as irrelevant treatment group.) Weighed their body weight every day, monitored the clinical scores of their limbs using double-blind method. Collected blood from orbital venous once a week, separated serum, and saved it in refrigerator at negative 80 degree.

Killed rat after treating 45 days, taken its ankle, HE staining. Separated lymphocytes from spleen, and detected content of splenic B cells by flow cytometry (B220 antibody detection).

Figure 9:
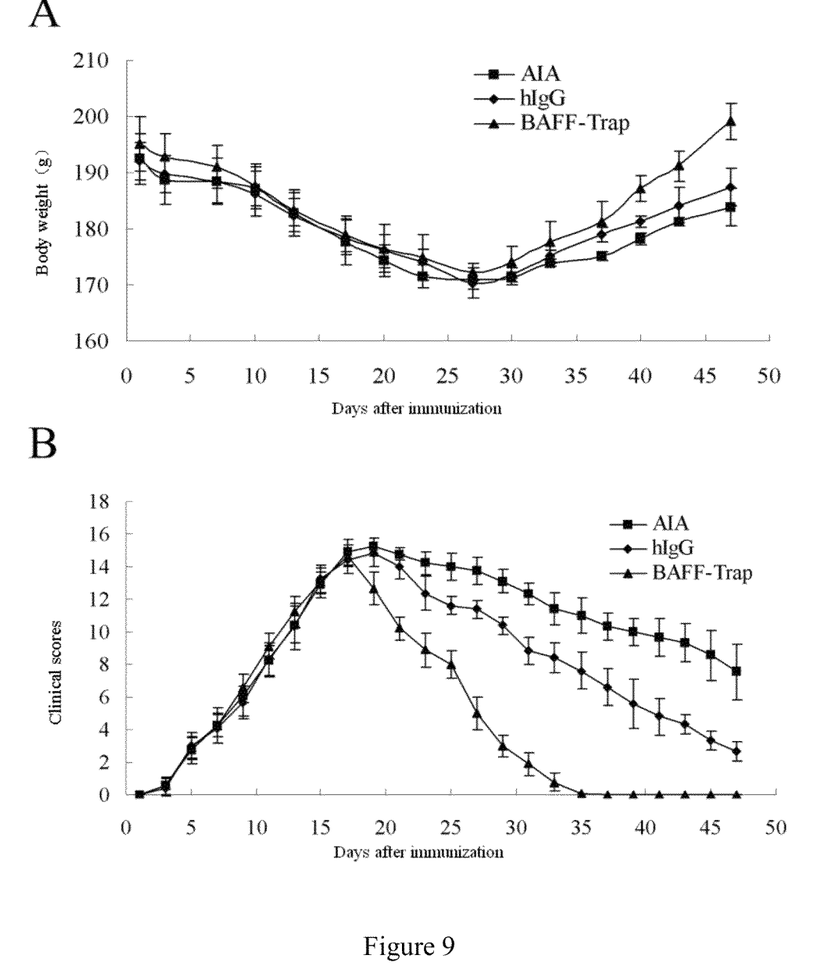
FIG. 9 shows the changes of body weight and clinical scores in rheumatoid arthritis model. A is weight change; B is clinical scores change.

The experimental results: Changes in the body weight and clinical score of each group of rats were shown as FIG. 9, the results showed: Started from the second day, the body weight of the rats began to decline, and treated from the 17th day, after a brief continued decline, reached a minimum at about 25th day, and then began to rise. But the pick-up rate of BAFF Trap group was higher than hIgG group and AIA group, and showed statistically significant ($P<0.05$) from the 43th day. Over time, the rheumatoid arthritis disease of model rats was gradually emerged and intensified, its clinical score also raised, on the 17th day arrived at 14±2. After then its clinical score gradually reduced, the reduction rate of the BAFF Trap group was significantly higher than the other two groups ($P<0.05$), and back to normal about on the 37th day, at this time the AIA group score was 10±1, hIgG group score was 6±1.

Figure 10:
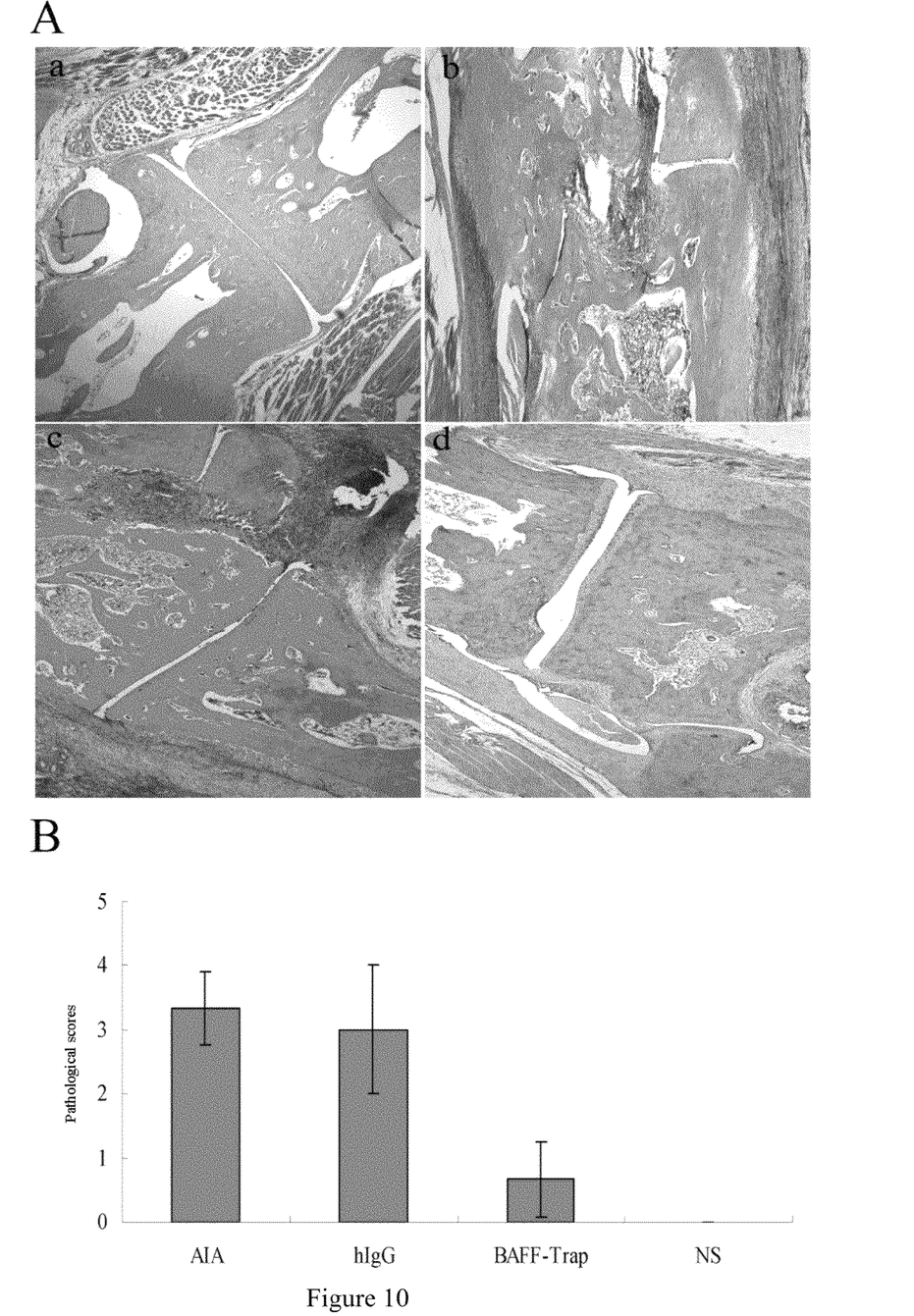
FIG. 10 shows the histopathological assessment of the ankle (HE, magnification: 10*40) and pathological score analysis. A is HE stain for the sections of ankle joints, wherein: a is normal rats group, b is model group, c is hIgG group, d is BT group; B shows pathological scores.

The HE staining result in every group was shown as FIG. 10A, in AIA group as well as hIgG group, lymphocyte infiltration, bone destruction and synovitis (in AIA group also can found bone fibrosis and pannus); Synovium integrity, repaying of the lymphocytes and repairing of damaged bone were visible in BT group, and it was similar with normal rat joint. Pathological scores results were shown as FIG. 10B), pathological scores of the AIA group and hIgG group were up to 4 points, pathology scores were significantly reduced ($P<0.05$) to normalize in the BT group.

Figure 11:
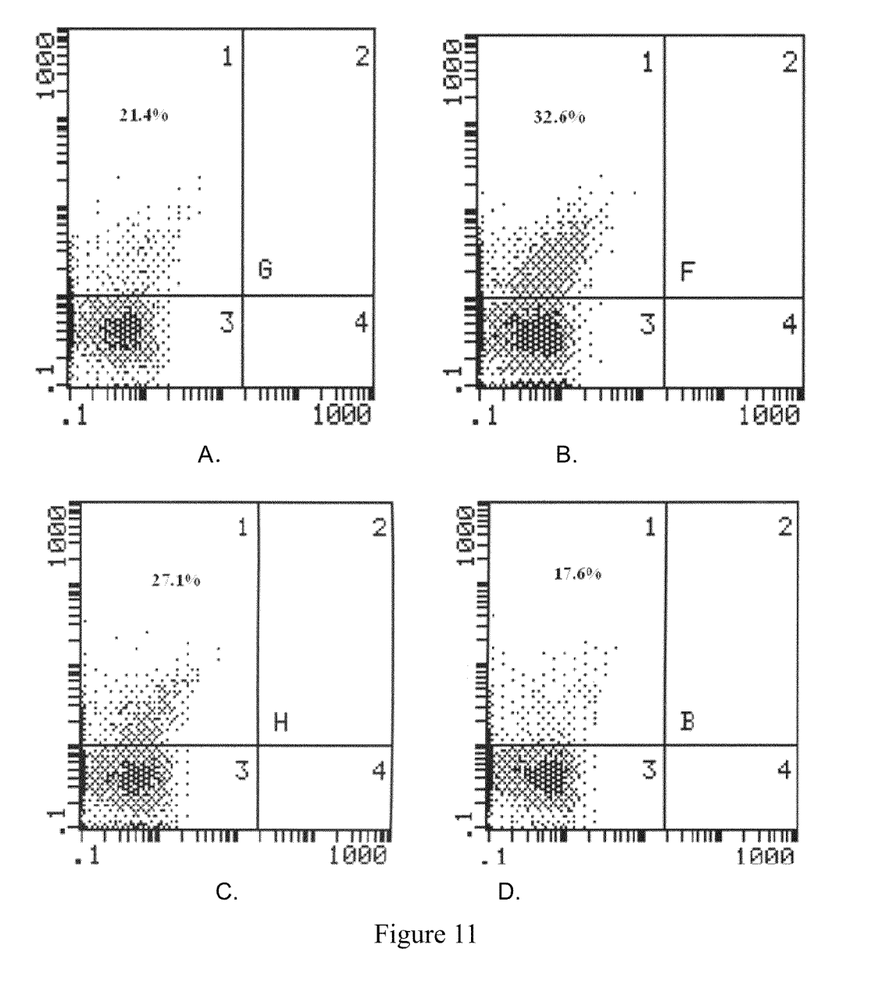
FIG. 11 shows the results for detecting of B220$^+$ B cell by flow cytometry. A: normal rats group; B: saline group; H: hIgG group; B: BT group.

The results for detecting of $B220^+$ B cells by flow cytometry were shown as FIG. 11. In BT group, the proportion of $B220^+$ B cells in rat splenocytes was 17.6%, much lower than that in the saline group (32.6%) and hIgG treatment group (27.1%). The results showed a significant difference ($P<0.01$) and were consistent with normal rats (21.4%).

The above examples show that the present invention successfully produced fusion protein BAFF Trap (BT) which can be used as a BAFF receptor antagonist. It has significant therapeutic effect on rat AIA model, providing a new effective choice for the treatment of autoimmune diseases.

REFERENCES

1. Moore P A, Belvedere O, Orr A, et al. BLyS: member of the tumor necrosis factor family and B lymphocyte stimulator. Science, 1999; 285: 260-2632.
2. Mackay F, Ambrose C: The TNF family members BAFF and APRIL: the growing complexity. Cytokine Growth Factor Rev 2003, 14(3-4):311-324
3. Schneider P, MacKay F, Steiner V, Hofmann K, Bodmer J L, Holler N, Ambrose C, Lawton P, Bixler S, Acha-Orbea H et al: BAFF, a novel ligand of the tumor necrosis factor family, stimulates B cell growth. J Exp Med 1999, 189(11):1747-1756.
4. Sutherland A P, Mackay F, Mackay C R: Targeting BAFF: immunomodulation for autoimmune diseases and lymphomas. Pharmacol Ther 2006, 112(3):774-786.
5. Scapini P, Nardelli B, Nadali G, et al. G-CSF-stimulated neutrophils are a prominent source of functional BLyS. J Exp Med, 2003; 197: 297-302.
6. Hymowitz S G, Patel D R, Wallweber H J, et al. Structures of APRIL-receptor complexes: like BCMA, TACI employs only a single cysteine-rich domain for high affinity ligand binding. J Biol Chem, 2005; 280: 7218-7227.
7. Kim H M, Yu K S, Lee M E, et al. Crystal structure of the BAFF-BAFF-R complex and its implications for receptor activation. Nat Struct Biol, 2003; 10: 342-348.

The invention claimed is:

1. A fusion protein comprising:
   (a) the amino acid sequence set forth in SEQ ID NO:1; or
   (b) a protein having at least 95% homology with SEQ ID NO: 1, wherein the protein functions as a B-cell activating factor (BAFF) antagonist.

2. The fusion protein according to claim 1, wherein the fusion protein comprises:
   (a) an amino acid sequence which is connected with an amino acid sequence of an Fc fragment of a human immunoglobulin to the C-terminus of the amino acid sequence of SEQ ID NO:1, or comprising (b) a protein having at least 95% homology with the Fc fragment connected SEQ ID NO:1,
wherein the protein functions as a BAFF antagonist.

3. The fusion protein according to claim 2, wherein the fusion protein comprises:
(a) the amino acid sequence set forth in SEQ ID NO:2, or
(b) a protein having at least 95% homology with SEQ ID NO: 2, wherein the protein functions as a BAFF antagonist.

4. The fusion protein according to claim 1, wherein its N-terminus is connected to a signal peptide.

5. The fusion protein according to claim 4, wherein the fusion protein comprises:
(a) the amino acid sequence as set forth in SEQ ID NO:3, or
(b) a protein having at least 95% homology with SEQ ID NO: 3, wherein the protein functions as a BAFF antagonist.

6. The fusion protein according to claim 2, wherein the protein is in the form of a dimmer.

7. A medicine for treating an autoimmune disease, comprising the fusion protein according to claim 1, a nucleotide sequence encoding the protein, or a gene vector containing the nucleotide sequence.

8. The medicine for the treatment of autoimmune diseases according to claim 7, wherein the autoimmune disease is rheumatoid arthritis, systemic lupus erythematosus or Sjogren syndrome.

9. A nucleotide sequence encoding the fusion protein according to claim 1.

10. The nucleotide sequence according to claim 9, comprising:
(a) SEQ ID NO: 10 or a degenerate sequence thereof; or
(b) a nucleotide sequence having at least 95% homology with SEQ ID NO: 10, and encoding a protein which functions as a BAFF antagonist.

11. The nucleotide sequence according to claim 10, comprising:
(a) SEQ ID NO:4 or a degenerate sequence thereof, or
(b) a nucleotide sequence having at least 95% homology with SEQ ID NO: 4, and encoding a protein which functions as a BAFF antagonist.

12. The nucleotide sequences according to claim 11, comprising:
(a) SEQ ID NO:5 or a degenerate sequence thereof, or
(b) a nucleotide sequence having at least 95% homology with SEQ ID NO: 5, and encoding a protein which functions as a BAFF antagonist.

13. A gene vector comprising the nucleotide sequence according to claim 9.

14. An isolated host cell comprising the gene vector according to claim 13.

15. A method for preparation of said fusion protein according to claim 1 comprising the steps of: loading genes encoding the fusion protein into an expression vector, transferring the expression vector into a host, cultivating and proliferating the host, and obtaining the fusion protein by isolation and purification of the host and/or its culture supernatant.

16. The method according to claim 15, wherein said expression vector is eukaryotic plasmid expression vector, adenovirus vector or adeno-associated virus vectors.

17. The method according to claim 16, wherein said host is a eukaryotic cell.

18. A method of using the fusion protein according to claim 1, for manufacturing a medicament for treatment of autoimmune diseases.

19. The method according to claim 18, wherein said autoimmune diseases are rheumatoid arthritis, systemic lupus erythematosus or Sjogren syndrome.

* * * * *

SEQUENCE LISTING

<160> NUMBER OF SEQ ID NOS: 10

<210> SEQ ID NO 1
<211> LENGTH: 87
<212> TYPE: PRT
<213> ORGANISM: artificial
<220> FEATURE:
<223> OTHER INFORMATION: B cell activating factor antagonist

<400> SEQUENCE: 1

Leu Ser Cys Arg Lys Glu Gln Gly Lys Phe Tyr Asp His Leu Leu Arg
1               5                   10                  15

Asp Cys Ile Ser Cys Ala Ser Ile Cys Gly Gln His Pro Lys Gln Cys
            20                  25                  30

Ala Tyr Phe Cys Glu Asn Lys Leu Arg Ser Pro Gly Arg Asp Ala Pro
        35                  40                  45

Ala Pro Thr Pro Cys Val Pro Ala Glu Cys Phe Asp Leu Leu Val Arg
    50                  55                  60

His Cys Val Ala Cys Gly Leu Leu Arg Thr Pro Arg Pro Lys Pro Ala
65                  70                  75                  80

Gly Ala Ser Ser Pro Ala Pro
                85

<210> SEQ ID NO 2

<211> LENGTH: 319
<212> TYPE: PRT
<213> ORGANISM: artificial
<220> FEATURE:
<223> OTHER INFORMATION: B cell activating factor antagonist

<400> SEQUENCE: 2

Leu Ser Cys Arg Lys Glu Gln Gly Lys Phe Tyr Asp His Leu Leu Arg
1               5                   10                  15

Asp Cys Ile Ser Cys Ala Ser Ile Cys Gly Gln His Pro Lys Gln Cys
            20                  25                  30

Ala Tyr Phe Cys Glu Asn Lys Leu Arg Ser Pro

```
          1               5                   10                  15
Val Thr Asn Ser Leu Ser Cys Arg Lys Glu Gln Gly Lys Phe Tyr Asp
                    20                  25                  30

His Leu Leu Arg Asp Cys Ile Ser Cys Ala Ser Ile Cys Gly Gln His
                35                  40                  45

Pro Lys Gln Cys Ala Tyr Phe Cys Glu Asn Lys Leu Arg Ser Pro Gly
            50                  55                  60

Arg Asp Ala Pro Ala Pro Thr Pro Cys Val Pro Ala Glu Cys Phe Asp
65                  70                  75                  80

Leu Leu Val Arg His Cys Val Ala Cys Gly Leu Leu Arg Thr Pro Arg
                    85                  90                  95

Pro Lys Pro Ala Gly Ala Ser Ser Pro Ala Pro Glu Pro Lys Ser Cys
                100                 105                 110

Asp Lys Thr His Thr Cys Pro Pro Cys Pro Ala Pro Glu Leu Leu Gly
            115                 120                 125

Gly Pro Ser Val Phe Leu Phe Pro Pro Lys Pro Lys Asp Thr Leu Met
        130                 135                 140

Ile Ser Arg Thr Pro Glu Val Thr Cys Val Val Val Asp Val Ser His
145                 150                 155                 160

Glu Asp Pro Glu Val Lys Phe Asn Trp Tyr Val Asp Gly Val Glu Val
                    165                 170                 175

His Asn Ala Lys Thr Lys Pro Arg Glu Glu Gln Tyr Asn Ser Thr Tyr
                180                 185                 190

Arg Val Val Ser Val Leu Thr Val Leu His Gln Asp Trp Leu Asn Gly
            195                 200                 205

Lys Glu Tyr Lys Cys Lys Val Ser Asn Lys Ala Leu Pro Ala Pro Ile
        210                 215                 220

Glu Lys Thr Ile Ser Lys Ala Lys Gly Gln Pro Arg Glu Pro Gln Val
225                 230                 235                 240

Tyr Thr Leu Pro Pro Ser Arg Asp Glu Leu Thr Lys Asn Gln Val Ser
                    245                 250                 255

Leu Thr Cys Leu Val Lys Gly Phe Tyr Pro Ser Asp Ile Ala Val Glu
                260                 265                 270

Trp Glu Ser Asn Gly Gln Pro Glu Asn Asn Tyr Lys Thr Thr Pro Pro
            275                 280                 285

Val Leu Asp Ser Asp Gly Ser Phe Phe Leu Tyr Ser Lys Leu Thr Val
        290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
                    325                 330                 335

Pro Gly Lys

<210> SEQ ID NO 4
<211> LENGTH: 951
<212> TYPE: DNA
<213> ORGANISM: artificial
<220> FEATURE:
<223> OTHER INFORMATION: nucleotide sequences encoding B cell activating
      factor antagonist

<400> SEQUENCE: 4
ctcagctgcc gcaaggagca aggcaagttc tatgaccatc tcctgaggga ctgcatcagc      60
tgtgcctcca tctgtggaca gcaccctaag caatgtgcat acttctgtga gaacaagctc     120
```

```
aggagcccag gcagggacgc gccagccccc acgccctgcg tcccggccga gtgcttcgac    180
ctgctggtcc gccactgcgt ggcctgcggg ctcctgcgca cgccgcggcc gaaaccggcc    240
ggggccagca gccctgcgcc cggatccgac aaaactcaca catgcccacc gtgcccagca    300
cctgaactcc tggggggacc gtcagtcttc ctcttccccc caaaacccaa ggacaccctc    360
atgatctccc ggacccctga ggtcacatgc gtggtggtgg acgtgagcca cgaagaccct    420
gaggtcaagt tcaactggta cgtggacggc gtggaggtgc ataatgccaa gacaaagccg    480
cgggaggagc agtacaacag cacgtaccgt gtggtcagcg tcctcaccgt cctgcaccag    540
gactggctga atggcaagga gtacaagtgc aaggtctcca acaaagccct cccagccccc    600
atcgagaaaa ccatctccaa agccaaaggg cagccccgag aaccacaggt gtacaccctg    660
cccccatccc gggatgagct gaccaagaac caggtcagcc tgacctgcct ggtcaaaggc    720
ttctatccca gcgacatcgc cgtggagtgg gagagcaatg ggcagccgga gaacaactac    780
aagaccacgc ctcccgtgct ggactccgac ggctccttct tcctctacag caagctcacc    840
gtggacaaga gcaggtggca gcaggggaac gtcttctcat gctccgtgat gcatgaggct    900
ctgcacaacc actacacgca gaagagcctc tccctgtctc cgggtaaatg a             951
```

<210> SEQ ID NO 5
<211> LENGTH: 1011
<212> TYPE: DNA
<213> ORGANISM: artificial
<220> FEATURE:
<223> OTHER INFORMATION: nucleotide sequences encoding B cell activating factor antagonist

<400> SEQUENCE: 5

```
atgtacagga tgcaactcct gtcttgcatt gcactaagtc ttgcacttgt cacgaattca     60
ctcagctgcc gcaaggagca aggcaagttc tatgaccatc tcctgaggga ctgcatcagc    120
tgtgcctcca tctgtggaca gcaccctaag caatgtgcat acttctgtga aaacaagctc    180
aggagcccag gcagggacgc gccagccccc acgccctgcg tcccggccga gtgcttcgac    240
ctgctggtcc gccactgcgt ggcctgcggg ctcctgcgca cgccgcggcc gaaaccggcc    300
ggggccagca gccctgcgcc cggatccgac aaaactcaca catgcccacc gtgcccagca    360
cctgaactcc tggggggacc gtcagtcttc ctcttccccc caaaacccaa ggacaccctc    420
atgatctccc ggacccctga ggtcacatgc gtggtggtgg acgtgagcca cgaagaccct    480
gaggtcaagt tcaactggta cgtggacggc gtggaggtgc ataatgccaa gacaaagccg    540
cgggaggagc agtacaacag cacgtaccgt gtggtcagcg tcctcaccgt cctgcaccag    600
gactggctga atggcaagga gtacaagtgc aaggtctcca acaaagccct cccagccccc    660
atcgagaaaa ccatctccaa agccaaaggg cagccccgag aaccacaggt gtacaccctg    720
cccccatccc gggatgagct gaccaagaac caggtcagcc tgacctgcct ggtcaaaggc    780
ttctatccca gcgacatcgc cgtggagtgg gagagcaatg ggcagccgga gaacaactac    840
aagaccacgc ctcccgtgct ggactccgac ggctccttct tcctctacag caagctcacc    900
gtggacaaga gcaggtggca gcaggggaac gtcttctcat gctccgtgat gcatgaggct    960
ctgcacaacc actacacgca gaagagcctc tccctgtctc cgggtaaatg a            1011
```

<210> SEQ ID NO 6
<211> LENGTH: 27
<212> TYPE: DNA
<213> ORGANISM: artificial
<220> FEATURE:

```
<223> OTHER INFORMATION: 5'primer to amplify IgG1 Fc fragment cDNA

<400> SEQUENCE: 6
cgggatccga caaaactcac acatgcc                                              27

<210> SEQ ID NO 7
<211> LENGTH: 33
<212> TYPE: DNA
<213> ORGANISM: artificial
<220> FEATURE:
<223> OTHER INFORMATION: 3' primer to amplify IgG1 Fc fragment cDNA

<400> SEQUENCE: 7
agctttgttt aaactcattt acccggagac agg                                       33

<210> SEQ ID NO 8
<211> LENGTH: 34
<212> TYPE: PRT
<213> ORGANISM: artificial
<220> FEATURE:
<223> OTHER INFORMATION: CRD2 of TACI

<400> SEQUENCE: 8

Cys Arg Lys Glu Gln Gly Lys Phe Tyr Asp His Leu Leu Arg Asp Cys
 1               5                  10                  15

Ile Ser Cys Ala Ser Ile Cys Gly Gln His Pro Lys Gln Cys Ala Tyr
            20                  25                  30

Phe Cys

<210> SEQ ID NO 9
<211> LENGTH: 17
<212> TYPE: PRT
<213> ORGANISM: artificial
<220> FEATURE:
<223> OTHER INFORMATION: CRD of Br3

<400> SEQUENCE: 9

Cys Val Pro Ala Glu Cys Phe Asp Leu Leu Val Arg His Cys Val Ala
 1               5                  10                  15

Cys

<210> SEQ ID NO 10
<211> LENGTH: 261
<212> TYPE: DNA
<213> ORGANISM: artificial
<220> FEATURE:
<223> OTHER INFORMATION: nucleotide sequences encoding B cell activating
      factor antagonist

<400> SEQUENCE: 10
ctcagctgcc gcaaggagca aggcaagttc tatgaccatc tcctgaggga ctgcatcagc          60
tgtgcctcca tctgtggaca gcaccctaag caatgtgcat acttctgtga gaacaagctc        120
aggagcccag gcagggacgc gccagccccc acgccctgcg tccggccgga gtgcttcgac        180
ctgctggtcc gccactgcgt ggcctgcggg ctcctgcgca cgccgcggcc gaaaccggcc        240
ggggccagca gccctgcgcc c                                                  261
```